United States Patent [19]

Weber

[11] Patent Number: 5,760,218

[45] Date of Patent: *Jun. 2, 1998

[54] DIAMINE SALTS OF CLAVULANIC ACID

[75] Inventor: Pieter Gijsbert Weber, Ridderkerk, Netherlands

[73] Assignee: Gist-Brocades N.V., Netherlands

[*] Notice: The portion of the term of this patent subsequent to Jun. 1, 2015, has been disclaimed.

[21] Appl. No.: 455,189

[22] Filed: May 31, 1995

Related U.S. Application Data

[60] Division of Ser. No. 338,585, Nov. 14, 1994, which is a continuation-in-part of Ser. No. 38,130, Mar. 26, 1993.

[51] Int. Cl.$^6$ .................................................. C07D 503/18
[52] U.S. Cl. ............................................................ 540/349
[58] Field of Search .............................................. 540/349

[56] References Cited

U.S. PATENT DOCUMENTS 5,310,898  5/1994  Copar .................................... 540/349

FOREIGN PATENT DOCUMENTS

| 0026044 | 4/1981 | European Pat. Off. . |
| 0387178 | 9/1990 | European Pat. Off. . |
| 0562583 | 9/1993 | European Pat. Off. . |
| 2517316 | 10/1975 | Germany . |
| 93-25557 | 12/1993 | WIPO . |

*Primary Examiner*—Mark L. Berch
*Attorney, Agent, or Firm*—Bierman, Muserlian and Lucas

[57] ABSTRACT

New diamine salts of clavulanic acid, pharmaceutical compositions comprising the same, and a new process using these diamine salts in the preparation of clavulanic acid and salts and esters thereof have been provided.

6 Claims, No Drawings

DIAMINE SALTS OF CLAVULANIC ACID

PRIOR APPLICATIONS

This application is a division of U.S. patent application Ser. No. 338,585 filed Nov. 14, 1994 which is a continuation-in-part of U.S. patent application Ser. No. 038,130 filed Mar. 26, 1993.

The present invention relates to new diamine salts of clavulanic acid, pharmaceutical compositions thereof, and to the use of these salts in the production of clavulanic acid and salts and esters thereof.

GB patent 1508977 discloses that clavulanic acid, which has the formula (I):

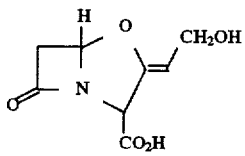

and its pharmaceutically acceptable salts and esters are anti-bacterial agents, able to enhance the effectiveness of penicillins and cephalosporins against many β-lactamase-producing bacteria.

U.S. Pat. No. 4,650,795 discloses a group of primary amine salts of clavulanic acid which give stable pharmaceutical compositions.

EP patent 26044 discloses the use of the t-butylamine salt as a useful intermediate in the preparation of clavulanic acid.

The non-prepublished EP patent application 562583 discloses the same use for N,N-diisopropylethylenediammonium di clavulanate and N,N-diethylethylenediammonium di clavulanate, both of the secondary, secondary type.

Surprisingly it has been found that tertiary, tertiary diamine salts of clavulanic acid have improved properties compared to the t-butyl amine salt of clavulanic acid mentioned above. For instance, large crystals of the mono salt of N,N,N',N'-tetramethyl-1,2-diaminoethane clavulanate can easily be precipitated in pure form. The salt is therefore a very useful intermediate in the preparation of clavulanic acid.

Accordingly, the present invention provides tertiary, tertiary diamine mono salts of the formula (IIa):

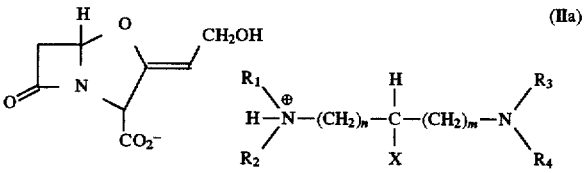

and tertiary, tertiary diamine di salts of formula (IIb):

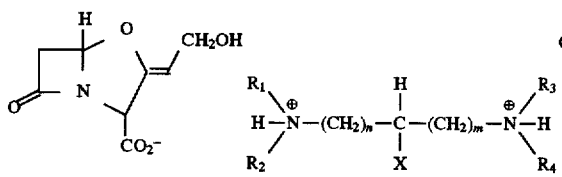

where $R_1$ and $R_2$ are each a (1–8C)alkyl, (3–8C)cycloalkyl or (3–8C)cycloalkyl (1–8C)alkyl group, optionally having one or more inert substituents or are interlinked to form a ring of 4–7 ring atoms; $R_3$ and $R_4$ are each a (1–8C)alkyl, (3–8C)cycloalkyl or (3–8C)cycloalkyl (1–8C)alkyl group, optionally having one or more inert substituents or are interlinked to form a ring of 4–7 ring atoms; X is hydrogen or a hydrogen bridge forming group; and m and n are each, independently, 0–5.

An alkyl group may be branched or straight chain.

A $C_1$ to $C_8$ alkyl group is preferably a $C_1$ to $C_4$ alkyl group, for example, methyl, ethyl, propyl, isopropyl, butyl, sec.butyl or tert.butyl, more preferably it is methyl.

A $C_3$ to $C_8$ cycloalkyl group is preferably a $C_5$ to $C_7$ cycloalkyl group, for example cyclopentyl, cyclohexyl or cycloheptyl.

Preferably, X is hydrogen, hydroxy or halogen, for instance bromine or chlorine. Most preferably, X is hydrogen or hydroxy.

Preferably n is from 0 to 3 and m is from 0 to 3, more preferably when X is hydrogen or hydroxy. Most preferably n=1, m is 0 and X is hydrogen or n is 1, m is 1 and X is hydroxy.

Suitably inert substituents include halogen, hydroxy, $C_1$ to $C_4$ alkyl, $C_1$ to $C_4$ alkoxyl, $C_1$ to $C_4$ acyloxyl and $C_1$ to $C_4$ esterified carboxyl.

A halogen atom is, for example, bromine, chlorine or fluorine, preferably, bromine or chlorine.

A $C_1$ to $C_4$ alkyl is preferably methyl or ethyl.

A $C_1$ to $C_4$ alkoxyl is preferably methoxyl or ethoxyl.

A $C_1$ to $C_4$ acyloxyl is preferably $C_1$ or $C_2$ acyloxyl.

A $C_1$ to $C_4$ esterified carboxyl is preferably $C_1$ or $C_2$ esterified carboxyl.

Generally, $R_1$, $R_2$, $R_3$ and $R_4$ have three substituents or fewer, preferably two substituents or fewer. Most preferably $R_1$, $R_2$, $R_3$ and $R_4$ have one substituent or are unsubstituted.

When $R_1$ and $R_2$ or $R_3$ and $R_4$ are interlinked to form a ring of 4 to 7 atoms, the ring consists preferably of carbon atoms and is most preferably saturated. Most preferably $R_1$, $R_2$, $R_3$ and $R_4$ are methyl.

Normally the amine of the formula (III):

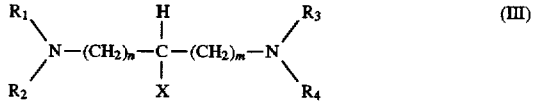

from which the salts of the formulae (IIa) and (IIb) are derivable is a pharmaceutically acceptable amine.

Preferably, the salts of the formulae (IIa) and (IIb) are derivable from N,N,N',N'-tetramethyl-1,2-diaminoethane, 1,3-bis(dimethylamino)-2-propanol, N,N,N',N'-tetramethyl-1,4-diaminobutane, N,N,N',N'-tetramethyl-1,6-diaminohexane, 1,2-dipiperidinoethane and dipiperidinomethane.

The present invention also provides a process for the preparation of a salt of formulae (IIa) or (IIb) which process comprises the reaction of clavulanic acid with diamine (III):

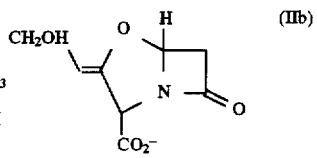

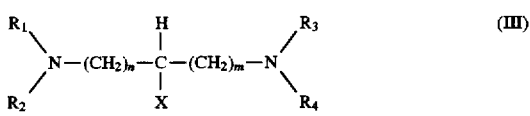

where $R_1$, $R_2$, $R_3$, $R_4$, X, m and n are as above defined. A diamine mono clavulanate will be formed when the amount of diamine is relatively high compared to that of clavulanic acid and the diamine di clavulanate will be formed when the amount of diamine is relatively low compared to that of clavulanic acid or a mixture of the same at a concentration in between.

The conditions when mono or diamine salts of clavulanic acid or a mixture of the same will be formed have not been investigated for each diamine, but it will be clear for someone skilled in the art that these will vary with the diamine applied.

The concentration of diamine present in the reaction mixture may be varied by, for example, varying the pH. At relatively high pH (dependent on the amine and the solvent used) more mono-protonated diamine (IIIa):

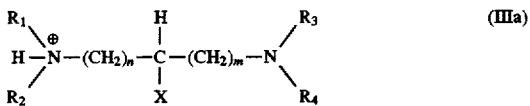

will be present and therefore more mono salt will be precipitated, and at relatively low pH more di-protonated diamine (IIIb):

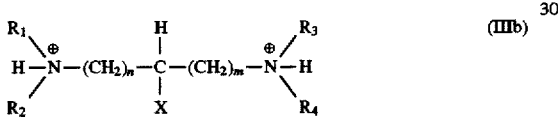

will be present and therefore more di salt will be precipitated.

The present invention further provides the use of diamine salts of clavulanic acid as defined above as an intermediate in the preparation of clavulanic acid and a pharmaceutically acceptable salt or ester thereof.

In another aspect the present invention provides a process for the preparation of clavulanic acid or a pharmaceutically acceptable salt or ester thereof which process comprises converting a diamine salt of clavulanic acid as defined above into clavulanic acid, generally by acidification, or a pharmaceutically acceptable salt or ester thereof, generally by adding a source of corresponding salt or ester forming compound.

In a further aspect the present invention provides a process for the purification of clavulanic acid or a pharmaceutically acceptable salt or ester thereof which process comprises:

i) contacting impure clavulanic acid in an organic solvent with diamine to form a salt;

ii) isolating the salt produced in step i); and iii) converting the isolated salt into clavulanic acid, generally by acidification, or a pharmaceutically acceptable salt or ester thereof, generally by adding a source of a corresponding salt or ester forming compound. For instance, potassium clavulanate is formed by adding potassium acetate or potassium ethylhexanoate.

Most suitably the formation of the diamine salts of clavulanic acid takes place in an organic solvent. Suitable solvents include non-hydroxylic solvents such as, for example, tetrahydrofuran, dioxane, ethyl acetate, methyl acetate, acetone, methylethylketone and the like solvent and mixtures thereof.

The reaction may be carried out at from about −50° C. to 40° C., most preferably from about 0° C. to 15° C.

The present invention also provides pharmaceutical compositions which comprise a salt of the formulae (IIa) and/or (IIb) and a pharmaceutically acceptable carrier.

Suitable forms of the compositions of this invention include tablets, capsules, reconstitutable powders and sterile forms suitable for injection or infusion. Such compositions may contain conventional pharmaceutically acceptable materials such as diluents, binders, colours, flavours, preservatives and disintegrants.

Injectable or infusible compositions of the salts of formulae (IIa) and (IIb) are particularly suitable as high tissue levels of the compound of clavulanic acid can occur after administration by injection or infusion. Thus, one preferred composition aspect of this invention comprises salts of the formulae (IIa) and (IIb) in sterile form.

Unit dose compositions comprising a salt of the formula (II) adapted for oral administration form a further preferred composition aspect of this invention.

The following examples will illustrate the invention. The pH value mentioned relates to this value measured with an Ingold electrode, type U402-S7/120, in the solvents applied.

EXAMPLES

Example 1

Comparison of Crystallization of Various Diamine Salts

A solution of potassium clavulanate in ice cold water was stirred with ethyl acetate under cooling with ice-water. With a solution of about 10% (w/w) sulphuric acid the pH was brought at about 2, the water layer separated and twice extracted with ethyl acetate. The collected extracts were dried with magnesium sulphate, filtered and washed with ethyl acetate, yielding a solution of clavulanic acid of about 2% (w/w). The clavulanic acid was diluted with an equal volume of acetone and diamine was added.

The results are summarized in Table I. The ratio moles diamine/moles clavulanic acid has been indicated in the last column. The tertiary, tertiary type diamine salts of clavulanic acid are present in the preferred crystal form only, viz. not in the form of an oil.

TABLE I

| Diamine | type[1] | crystals | oil | diamine |
|---|---|---|---|---|
| N,N,N',N'-tetramethyl-1,2-diaminoethane | t, t | + | − | 1.90 |
| N,N,N',N'-tetramethyl-1,2-diaminoethane | t, t | + | − | 0.68 |
| N,N,N',N'-tetramethyl-1,3-diaminopropane | t, t | + | − | 1.89 |
| 1,3-bis(dimethylamino)-2-propanol | t, t | + | − | 1.74 |
| N,N,N',N'-tetramethyl-1,4-diaminobutane | t, t | + | − | 1.34 |
| N,N,N',N'-tetramethyl-1,6-diaminohexane | t, t | + | − | 1.84 |
| 1,2-dipiperidinoethane | t, t | + | − | 2.70 |
| 1,2-diaminoethane | p, p | + | + | 3.98 |
| 1,3-diaminopropane | p, p | + | + | 1.69 |
| 1,6-diaminohexane | p, p | − | + | 1.69 |
| 1,10-diaminodecane | p, p | − | + | 1.46 |
| N-methyl-1,3-diaminopropane | p, s | − | + | 1.69 |
| N,N-dimethyl-1,3-diaminopropane | p, t | − | + | 1.86 |
| N,N-dimethyl-1,2-diamino- | p, t | − | + | 1.69 |

TABLE I-continued

| Diamine | type[1] | crystals | oil | diamine |
|---|---|---|---|---|
| ethane | | | | |
| piperazine | s, s | – | + | 1.20 |
| N-methylpiperazine | s, t | – | + | 1.20 |
| N,N-diethyl-1,2-diaminoethane | p, t | – | – | 0.81 |
| N-(2-aminoethyl)-morfoline | p, t | – | – | 1.20 |
| dipiperidinomethane | t, t | + | – | 14.92 |

[1]p: primary; s: secondary; t: tertiary

Example 2

Preparation of N,N,N',N'-tetramethyl-1,2-diaminoethane Mono Clavulanate from Ethyl Acetate/Acetone Solution A clavulanic acid extract in dry ethyl acetate (828 g containing 18 g of clavulanic acid/kg prepared according to example 1) was added in 20 min to 1 l of acetone while cooling (8° C.) and keeping the pH at 9 with N,N,N',N'-tetramethyl-1,2-diaminoethane (TMEDA, 19.18 g, viz. a molar ratio of 2.2 related to clavulanic acid). Stirring was continued at 10° C. for 1 hr. The precipitate was filtered off and washed with 100 ml of acetone and dried in vacuum at 35° C. to yield 20.09 g of TMEDA mono clavulanate (large crystals). The mother liquor (1642 g) contained about 1.12 g of clavulanic acid.

NMR (DMSO-d6): 2.37 ppm, N—$CH_3$ (s, 12H); 2.70 ppm, N—$CH_2$ (s, 4H); 2.95 ppm, C6-βH (d, 1H); 3.49 ppm, C6-αH (dd, 1H); 3.99 ppm, $CH_2OH$ (m, 2H); 4.60 ppm, C3—H (s, 1H); 4.66 ppm, =C—H (tr, 1H); 5.58 ppm, C5-H (d, 1H).

To 1 g of this TMEDA mono clavulanate 200 ml of a mixture of ethyl acetate/acetone (1/1 v/v) comprising 1 ml of TMEDA was added. After stirring during 1 hr at room temperature and filtrating the solution, the filtrate was slowly evaporated, resulting in large crystals.

All parameters were obtained by least squares from 2 θ values for reflections measured on a diffractometer under the following experimental conditions:

CAD 4 Rf Nonius
θ=30°
Mo—Kα radiation
λ=0.70145 Å.

The salt ($C_{14}H_{25}N_3O_5$, group 1 $C_8H_9NO_5$ and group 2 $C_6H_{16}N_2$; Mw=315.37) crystallizes in the orthorhombic space group $P2_12_12_1$ with a=8.268(1), b=9.929(7) and c=20.221(2) Å. α, β and γ=90°.
R=0.206 for 2747 reflections.
z=4.

The molecules are bonded via a strong hydrogen bond (2.65(1) Å) between N(2) and O(3). The C(6)—O(2) and C(6)—O(3) distances are 1.20(1) and 1.275(9) Å, respectively, indicating a partial single bond character between C(6)—O(3).

The atom coordinates are shown in Table II:

TABLE II

| | x/a | y/b | z/c | sigx | sigy | sigz |
|---|---|---|---|---|---|---|
| C1 | .73451 | .61143 | .51083 | .00109 | .00094 | .00039 |
| C2 | .72822 | .73554 | .46864 | .00099 | .00085 | .00037 |
| C3 | .77712 | .80814 | .53160 | .00099 | .00091 | .00038 |
| C4 | .62466 | .80092 | .62729 | .00091 | .00081 | .00035 |
| C5 | .74057 | .68316 | .63023 | .00092 | .00079 | .00033 |
| C6 | .87476 | .71031 | .68279 | .00092 | .00083 | .00034 |
| C7 | .51426 | .83929 | .67005 | .00099 | .00089 | .00039 |
| C8 | .40390 | .95903 | .66482 | .00104 | .00092 | .00040 |
| C9 | .94385 | .09742 | .62131 | .00161 | .00119 | .00049 |
| C10 | .77651 | .20910 | .70628 | .00115 | .00169 | .00053 |
| C11 | 1.36988 | .31842 | .57368 | .00165 | .00182 | .00077 |
| C12 | 1.28231 | .43860 | .66215 | .00211 | .00137 | .00068 |
| C13 | 1.07802 | .36142 | .57942 | .00185 | .00171 | .00077 |
| C14 | .92742 | .34721 | .63555 | .00146 | .00127 | .00064 |
| N2 | .92914 | .21251 | .66938 | .00078 | .00080 | .00031 |
| N3 | 1.22359 | .33641 | .61693 | .00112 | .00091 | .00037 |
| O1 | .69320 | .49552 | .50870 | .00079 | .00072 | .00030 |
| O2 | .98843 | .77785 | .66617 | .00065 | .00064 | .00027 |
| O3 | .84583 | .65805 | .73917 | .00070 | .00070 | .00025 |
| O4 | .64046 | .86534 | .56720 | .00068 | .00060 | .00026 |
| O5 | .42783 | 1.04139 | .72369 | .00074 | .00075 | .00031 |
| N1 | .80549 | .68028 | .56442 | .00069 | .00067 | .00028 |
| H21 | .82775 | .76503 | .43642 | .00679 | .00618 | .00278 |
| H22 | .60667 | .74308 | .44395 | .00696 | .00637 | .00278 |
| H31 | .87967 | .86532 | .53289 | .00739 | .00655 | .00279 |
| H51 | .69414 | .59219 | .64269 | .00759 | .00616 | .00283 |
| H71 | .51235 | .78214 | .69945 | .00721 | .00654 | .00273 |

Example 3

Preparation of N,N,N',N'-tetramethyl-1,2-diaminoethane Mono Clavulanate From Ethyl Acetate Solution A solution of clavulanic acid in ethyl acetate (75 g, containing about 20 g of clavulanic acid/kg) was added in 10 min to 75 ml of ethyl acetate at 8° C. while stirring and keeping the pH between 8 and 9 with N,N,N',N'-tetramethyl-1,2-diaminoethane (TMEDA, 5.11 g, viz. a molar ratio of 8 related to clavulanic acid). Stirring was continued for 0.5 hr and the precipitate was filtered off, washed with ethyl acetate and dried in vacuum at 35° C. to give 2.62 g of TMEDA mono clavulanate (large crystals). The mother liquor (155 g) contained 0.03 g of clavulanic acid.

NMR (DMSO-d6): 2.38 ppm, N—$CH_3$ (s, 12H); 2.70 ppm, N—$CH_2$ (s, 4H); 2.93 ppm, C6-βH (d, 1H); 3.48 ppm, C6-αH (dd, 1H); 3.98 ppm, $CH_2OH$ (m, 2H); 4.58 ppm, C3-H (s, 1H); 4.65 ppm, =C—H (tr, 1H); 5.58 ppm, C5-H (d, 1H).

Example 4

Preparation of N,N,N',N'-tetramethyl-1,2-diaminoethane Di Clavulanate From Ethyl Acetate/Acetone Solution A solution of clavulanic acid in ethyl acetate (200 ml containing 1.1 g of clavulanic acid) was added in 10 min to 200 ml of cold acetone (10° C.) while stirring and keeping the pH between 7.5 and 8 with N,N,N',N'-tetramethyl-1,2-diaminoethane (TMEDA, 0.64 g, viz. a molar ratio of 1.45 related to clavulanic acid). Stirring was continued for 0.5 hr and the precipitate was filtered off, washed with acetone and dried in vacuum at 35° C. to give 1.24 g of TMEDA di clavulanate (crystals in needle form). The mother liquor (337 g) contained 0.11 g of clavulanic acid.

NMR (DMSO-d6): 2.45 ppm, N—$CH_3$ (s, 12H); 2.80 ppm, N—$CH_2$ (s, 4H); 2.99 ppm, C6-βH (d, 2H); 3.53 ppm, C6-αH (dd, 2H); 3.99 ppm, $CH_2OH$ (m, 4H); 4.69 ppm, =C—H (tr, 2H); 4.76 ppm, C3-H (s, 2H); 5.61 ppm, C5-H (d, 2H).

Example 5

Preparation of 1,3-bis(dimethylamino)-2-propanol Mono Clavulanate

A solution of clavulanic acid in ethyl acetate (100 g, containing 20 g clavulanic acid/kg) was added over a period of 10 min to 100 ml of acetone while stirring at 8° C. and keeping the pH between 8.5 and 8.7 with 1,3-bis (dimethylamino)-2-propanol (2.54 g, viz. a molar ratio of 1.74 related to clavulanic acid). Stirring was continued for 0.25 hr and the precipitate was filtered off and washed with 50 ml of a 1/1 mixture of acetone and ethyl acetate and with acetone. Drying in vacuum at room temperature yielded 1.82 g of 1,3-bis(dimethylamino)-2-propanol mono clavulanate with a purity of 25.6% as free acid.

NMR (DMSO-d6): 2.41 ppm, N—$CH_3$ (s, 12H); 2.50 ppm, N—$CH_2$ (dABq, 4H, J 12.6 Hz, J 4.8 Hz); 2.61 ppm, N—$CH_2$ (dABq, 4H, J 12.6 Hz, J 4.8 Hz); 2.94 ppm, C6-βH (d, 1H, J 16.5 Hz); 3.49 ppm, C6-αH (dd, 1H, J 16.5 Hz, J 2.7 Hz); 3.96 ppm $CH_2OH$, CHOH (m, 3H); 4.58 ppm, C3-H (s, 1H); 4.64 ppm =C—H (tr, 1H, J 6.8 Hz); 5.57 ppm, C5-H (d, 1H, J 2.6 Hz).

Example 6

Conversion of N,N,N',N'-tetramethyl-1,2-diaminoethane Mono Clavulanate Into Potassium Clavulanate 30 ml of a 0.35M potassium acetate solution (solvent isopropylalcohol and 1% (w/v) water) was added dropwise to a suspension of 2 g of N,N,N',N'-tetramethyl-1,2-diamminoethane mono clavulanate (content 68.6%) in 50 ml of isopropanol. After 0.75 hr stirring at room temperature the precipitate was filtered, washed with 10 ml of isopropanol and dried in vacuum at 35° C. yielding 1.44 g of crystalline potassium clavulanate with a content of 87% (clavulanic acid) and about 1.5% potassium acetate (HPLC analysis). The mother liquor contained about 0.06 g of clavulanic acid.

Example 7

Conversion of N,N,N',N'-tetramethyl-1,2-diaminoethane Di Clavulanate Into Potassium Clavulanate 4.5 ml of a 2M solution of potassium 2-ethyl-hexanoate in isopropanol was added to a stirred solution of 2 g of N,N,N',N'-tetramethyl-1,2-diaminoethane di clavulanate (purity 75.8% calculated as the free acid) in 20 ml of isopropanol and 2 ml of water at room temperature. After stirring for 0.25 hr the precipitate was filtered off and washed with 5 ml of isopropanol. Drying in vacuum at room temperature gave 0.30 g of potassium clavulanate with a purity of 83.6% calculated as the free acid.

A further 2.5 ml of a 2M solution of potassium 2-ethyl-hexanoate in isopropanol was added to the mother liquor and stirring was continued. The precipitate was filtered off, washed with 5 ml of isopropanol and dried to give 0.68 g of potassium clavulanate with a purity of 82.3% calculated as the free acid.

Example 8

Conversion of 1,3-bis(dimethylamino)-2-propanol Mono Clavulanate Into Potassium Clavulanate 1.6 ml of a 2M solution of potassium 2-ethyl-hexanoate in isopropanol was added to a stirred solution of 1 g of 1,3-bis(di-methylamino)-2-propanol mono clavulanate in 19 ml of isopropanol and 1 ml of water at room temperature. After stirring for 0.25 hr the precipitate was filtered off and washed with 15 ml of isopropanol. Drying in vacuum at room temperature gave 0.38 g of potassium clavulanate with a purity of 80% as free acid.

I claim:

1. A salt of clavulanic acid of the formula

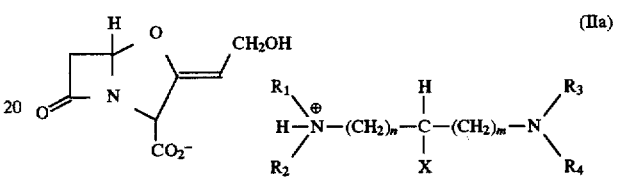

(IIa)

wherein $R_1$, $R_2$, $R_3$ and $R_4$ are individually selected from the group consisting of alkyl of 1 to 8 carbon atoms, cycloalkyl of 3 to 8 carbon atoms and cycloalkyl alkyl of 3 to 8 cycloalkyl carbon atoms and alkyl of 1 to 8 carbon atoms, all optionally substituted with 1 to 3 members of the group consisting of halogen, —OH, lower alkoxy and carboxy esterified with lower alkyl, X is hydroxy or halogen; and m and n are each, independently, 0–5 and n+m is at most 9.

2. A salt of clavulanic acid of the formula (IIa):

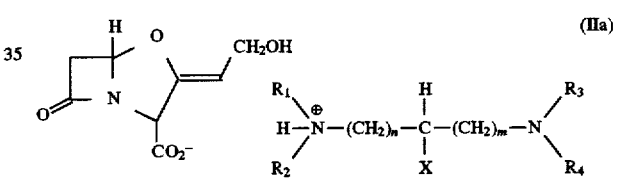

(IIa)

wherein $R_1$, $R_2$, $R_3$ and $R_4$ are individually selected from the group consisting of alkyl of 1 to 8 carbon atoms, cycloalkyl of 3 to 8 carbon atoms and cycloalkyl alkyl of 3 to 8 cycloalkyl carbon atoms and alkyl of 1 to 8 carbon atoms, all optionally substituted with 1 to 3 members of the group consisting of halogen, —OH, lower alkoxy and carboxy esterified with lower alkyl; X is hydrogen, and m and n are each, independently, 0–5.

3. A mono salt of clavulanic acid of claim 2 where X is hydrogen, n is 1 and m is 0.

4. A mono salt of clavulanic acid of claim 1 wherein X is hydroxy, n is 1 and m is 1.

5. A mono salt of clavulanic acid of claim 2 wherein $R_1$, $R_2$, $R_3$ and $R_4$ are methyl, X is hydroxy, n is 1 and m is 1.

6. A mono salt of clavulanic acid of claim 2 where $R_1$, $R_2$, $R_3$ and $R_4$ are methyl.

* * * * *